(12) United States Patent
Jaeger et al.

(10) Patent No.: US 7,041,845 B2
(45) Date of Patent: May 9, 2006

(54) PROCESS FOR PREPARING OPTICALLY ACTIVE DIHYDROPYRONES

(75) Inventors: Burkhard Jaeger, Bingen (DE); Markus Sauter, Gensingen (DE); Juergen Schroeder, Mainz (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 90 days.

(21) Appl. No.: 10/727,225

(22) Filed: Dec. 3, 2003

(65) Prior Publication Data
US 2004/0133032 A1 Jul. 8, 2004

(30) Foreign Application Priority Data
Dec. 10, 2002 (DE) ................................ 102 57 761

(51) Int. Cl.
C07C 69/76 (2006.01)
(52) U.S. Cl. ........................................................ 560/56
(58) Field of Classification Search ................... 560/53
See application file for complete search history.

(56) References Cited

U.S. PATENT DOCUMENTS
2002/0161037 A1 10/2002 Meyer et al.

FOREIGN PATENT DOCUMENTS
DE 10108471 C1 11/2002
WO WO 9819997 5/1998

OTHER PUBLICATIONS

Kumar et al, Journal of Chromatography, vol. 678 (1994) pp. 259-263.*
Tabuchi et al, Tetrahedron Letters, vol. 34(14) pp. 2327-2230.*
Francotte ER, Enantioselective chromatography as a powerful alternative for the preparation of drug enantiomers, J Chromatogr A. Jan. 12, 2001;906(1-2):379-97.
Web page located at http://www.raell.demon.co.uk/chem/CHIbook/Chiral.htm, 1999.
Practical HPLC method development, 2nd Edition, Synder, Lloyd R; Kirkland, J. J; Glajch, Joseph L.; New York : John Wiley & Sons, c1997, pp. 586-581.
S. Levin and S. Abu-Lafi, The Role of Enantioselective Liquid Chromatographic Separations Using Chiral Stationary Phases in Pharmaceutical Analysis, in Advances in Chromatography. E. Grushka and P. R. Brown, Eds., Marcel Dekker Inc.; NY. vol. 33, 1993: 233-266.
Steve R. Turner et al; Tipranavir (PNU-140690): A Potent, Orally Bioavailable Nonpeptidic HIV Protease Inhibitor of the 5,6-Dihydro-4-hydroxy-2-pyrone sulfonamide Class; J. Med. Chem. (1998) vol. 41 pp. 3467-3476; American Chemical Society.
Copy of International Search Report Reference #PCT/EP 03/13851.

* cited by examiner

Primary Examiner—J. Parsa
(74) Attorney, Agent, or Firm—Michael P. Morris; Mary-Ellen M. Devlin; Alan R. Stempel

(57) ABSTRACT

The invention relates to a process for preparing optically active 5-hydroxy-3-ketoesters of formula A1 or A2,

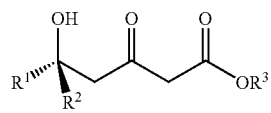

A1 or A2 or one of the tautomers thereof,
the use thereof for preparing optically active dihydropyrones of formula B,

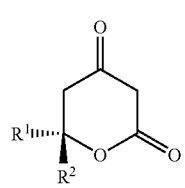

B and the use of the dihydropyrones of formula B thus prepared as starting compounds for preparing pharmaceutically active compounds, particularly Tipranavir.

9 Claims, 1 Drawing Sheet

PROCESS FOR PREPARING OPTICALLY ACTIVE DIHYDROPYRONES

FIELD OF THE INVENTION

The present invention relates to a process for preparing optically active 5-hydroxy-3-ketoesters, the use thereof for preparing optically active dihydropyrones and the use of the dihydropyrones as starting compounds for preparing pharmaceutically active compounds.

BACKGROUND TO THE INVENTION

As enantiomers differ only slightly in their physical properties but substantially in their physiological activities it is of fundamental importance for certain applications to obtain the enantiomeric forms separately from one another. This is particularly important in the field of pharmaceuticals. The main goal is to produce compounds which are as enantiomerically pure as possible as an enantiomer can enter into various unforeseeable interactions with other chiral compounds. Nature has developed special chiral catalysts such as enzymes for this purpose which operate enantioselectively with a high degree of activity. By contrast, attempts are made in preparative chemistry to provide stereo selective methods of synthesis which result in only one isomer of high optical purity in a high yield. This can only be achieved in exceptional cases. Another possibility consists of physical methods of separation by means of which the enantiomers produced can be separated.

A frequently used method of enantiomer separation is so called racemate cleaving, i.e. the breaking down of a mixture of equal parts of both enantiomers into the optically active components. One of the most common methods of enantiomer separation is the chemical cleaving of racemic mixtures in which either a racemic acid which is to be separated into the enantiomers if reacted with an optically active base or an optically active acid is reacted with a racemic base, forming a salt. This produces diastereomers which can be separated from one another on the basis of their different solubilities.

Thus, for example, U.S. Pat. No. 4,661,628 describes a method of separating racemic mixtures of α-naphthylpropionic acids by the addition of a β-aminoalcohol, as a result of which the diastereomeric amides formed can be separated by fractional crystallisation and subsequently changed back into the optically active acids by hydrolysis. This separation of the enantiomers is essential as only one of the two isomers has an anti-inflammatory activity. It is internationally known by the name Naproxen.

Also, known physical methods are used for racemate cleaving. Thus, in gas chromatography, thin layer chromatography, HPLC, liquid-liquid extraction or distribution, interactions such as hydrogen bridge bonds, ligand exchange and the formation of metal or charge transfer complexes are used to separate the enantiomers. In order to separate enantiomers by chromatographic methods generally optically active adsorbence are used, while chiral stationary or mobile phases are used. A known example is the racemate cleaving of Tröger's base using lactose.

Enantiomer separation is of great importance particularly in the pharmaceutical field in which specific compounds are of interest, i.e. only those enantiomeric forms which have the desired pharmacological and toxicological effects. For example, the enantiomers of the 5-hydroxy-3-ketoesters or the 5,6-dihydro-4-hydroxy-2-pyrones which can be obtained from them are important structural elements in a number of pharmaceutically active compounds, the class of the 5,6-dihydro-4-hydroxy-2-pyrone-sulphonamides being particularly important as they are used as non-peptidic HIV protease inhibitors. A particularly effective example of a potent HIV protease inhibitor of this category which is orally bioavailable is the compound Tipranavir (PNU-140690), which has the following structure:

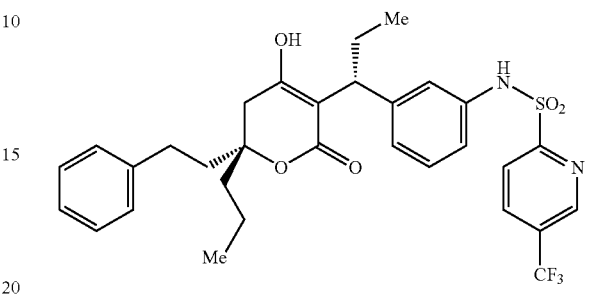

This and other structurally similar compounds are known from the prior art (cf. for example *J. Med. Chem.* 1998, 41, 3467–3476).

A key step in the synthesis of the above-mentioned and structurally similar compounds is the reaction of 5,6-dihydro-4-hydroxy-2-pyrones 1 with suitably substituted carbonyl compounds 2 to form the condensation products 3, as illustrated in the following Diagram 1:

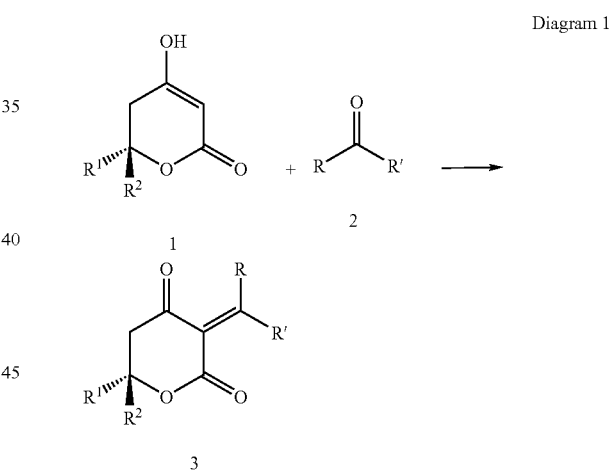

Diagram 1

The meaning of the different groups $R^1$ and $R^2$ being given in the description of the present invention. The groups R and R' are variable and are determined by the substitution pattern for the target compounds in question as are apparent from the prior art.

One method of preparing or obtaining enantiomers of the optically active dihydropyrones is already known from the prior art. Thus, WO 02/068404 A1 describes a process of this kind in which first of all suitably substituted carbonyl compounds are reacted with an acetoacetic acid derivative in the presence of organic or inorganic bases to form a racemic mixture of 5,6-dihydro-4-hydroxy-2-pyrones. The racemic mixture obtained is then converted with a chiral aminoalcohol into the salts, while depending on the choice of the aminoalcohol the desired salts of the R- or S- configuration can be crystallised out and the remaining enantiomer remains in solution.

The invention is thus based on the problem of providing a process, as a further development of the prior art, which allows 1 (B) to be synthesised in high yields, with a high enantiomeric purity, with the least possible technical expenditure and a high space/time yield. This process should also be suitable for use on a larger industrial scale, i.e. it should be cheap and therefore economical to carry out. Moreover, the compounds 1 (B) provided according to the invention, which are of central importance in the synthesis of the above-mentioned pharmaceutically active compounds, should not lose the chiral information contained in the starting compounds in the course of the subsequent reaction or reactions but this information should be retained in any case so that the desired properties are achieved.

DETAILED DESCRIPTION OF THE INVENTION

Figure 1:
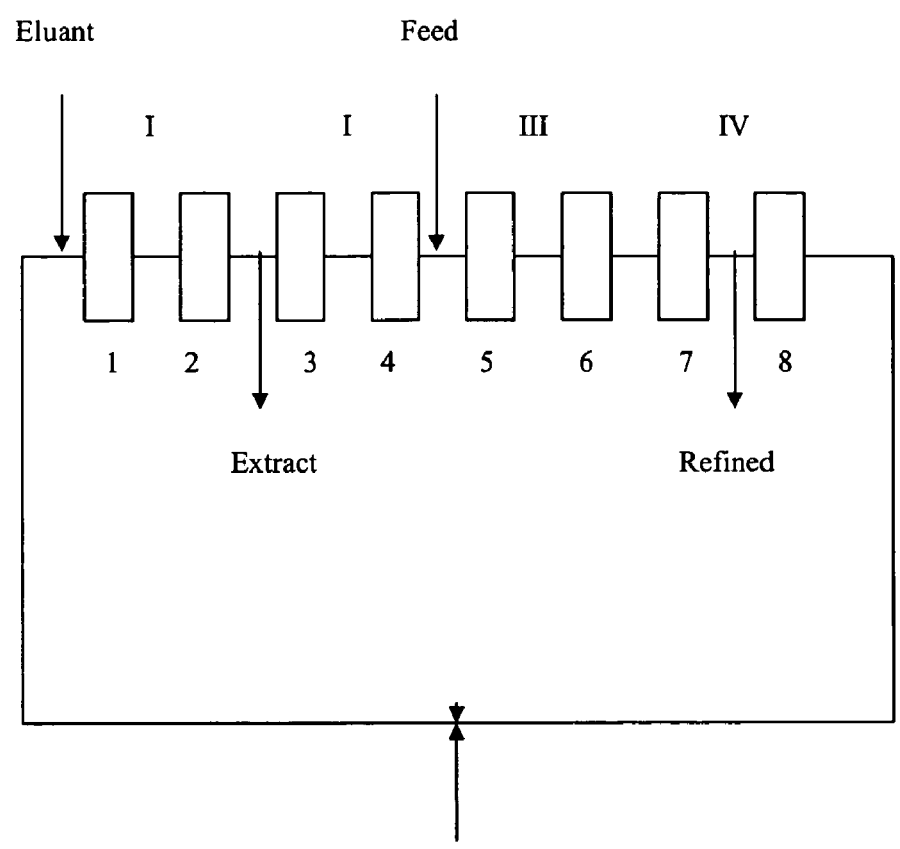
FIG. 1 shows the diagrammatic structure of an SMB (Simulated Moving Bed) System which may advantageously be used to carry out the process according to the invention.

Surprisingly, it has been found that the problem of the present invention as described above can be solved by means of three-step process, i.e. in step (1) preparing a racemic mixture of a 5-hydroxyketoester A, separating this racemate in step (2) into the two enantiomeric forms A1 and A2 by chromatography on a chiral carrier material and finally in step (3) carrying out conventional cyclisation to obtain the desired chiral 5,6-dihydro-4-hydroxy-2-pyrone B. This is shown in Diagram 2 below:

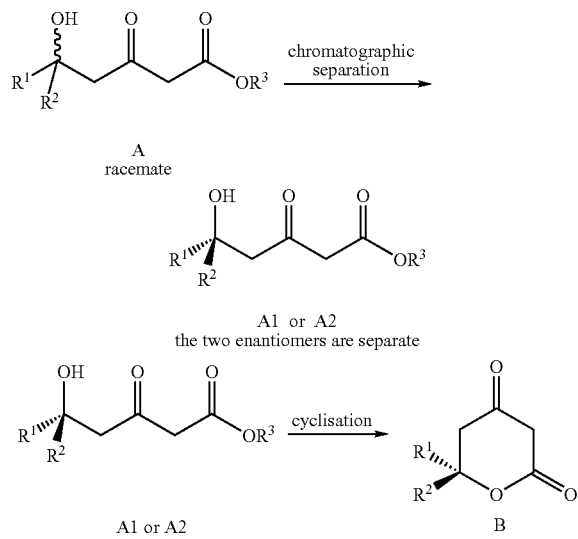

Diagram 2

Within the scope of the present invention a reference to compounds of formula 1, A1, A2 or B is to be taken as a reference to the compound in an optically active form. The optically active form in question is obtained from the definition of the groups $R^1$ and $R^2$. Racemic mixtures are designated by formula A, as already stated above. A reference to 1 or B also includes the tautomeric forms.

Accordingly, the present invention relates to a process for preparing an optically active 5-hydroxy-3-ketoester of formula A1 or A2

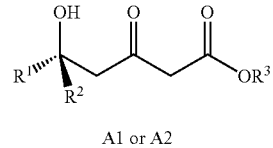

A1 or A2 or one of the tautomers thereof, wherein $R^1$ and $R^2$ independently of each other represent hydrogen or a group which is selected from among $C_1-C_8$-alkyl, $C_3-C_8$-cycloalkyl, $C_6-C_{10}$-aryl and $C_1-C_8$-alkylene-$C_6-C_{10}$-aryl, optionally with one, two or three substituents, selected from among hydroxy, halogen, $C_1-C_4$-alkoxy and $CF_3$, where $R^1$ and $R^2$ do not simultaneously have the same meaning, and $R^3$ denotes a group selected from among $C_1-C_8$-alkyl, $C_1-C_4$-Haloalkyl, $C_6-C_{10}$-aryl-$C_1-C_8$-alkylene and trihydrocarbylsilyl; by separating a racemic mixture of a 5-hydroxy-3-ketoester of formula A

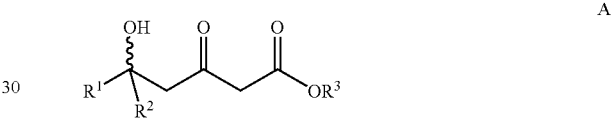

wherein $R^1$, $R^2$ and $R^3$ are as hereinbefore defined, into the two enantiomeric 5-hydroxy-3-ketoesters A1 and A2 with preparative high performance liquid chromatographyy (HPLC) over a chiral carrier material.

The present invention also relates to the use of the enantiomeric 5-hydroxy-3-ketoesters A1 and A2 thus produced for preparing an optically active dihydropyrone of formula B

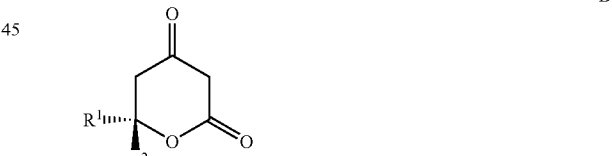

or one of the tautomers thereof, wherein $R^1$ and $R^2$ independently of each another denote hydrogen or a group selected from among $C_1-C_8$-alkyl, $C_3-C_8$-cycloalkyl, $C_6-C_{10}$-aryl and $C_1-C_8$-alkylene-$C_6-C_{10}$-aryl, optionally with one, two or three substituents, selected from among hydroxy, halogen, $C_1-C_4$-alkoxy and $CF_3$, wherein $R^1$ and $R^2$ do not simultaneously have the same meaning, by cyclising one of the enantiomeric 5-hydroxy-3-ketoesters A1 or A2 by known methods to form an optically active dihydropyrone of formula B.

According to a preferred embodiment of the invention the groups $R^1$ and $R^2$ independently of one another are selected from among methyl, ethyl, propyl, butyl, phenyl, benzyl, phenylethyl and phenylpropyl, optionally mono substituted by a group selected from among hydroxy, fluorine, chlorine, bromine, method, ethoxy and $CF_3$, with the proviso that $R^1$ and $R^2$ cannot simultaneously have the same meaning. Particularly preferred for $R^1$ and $R^2$ are the groups methyl, ethyl, propyl, butyl, benzyl, phenylethyl and phenylpropyl, of which propyl and phenylethyl are particularly preferred. According to a particularly preferred embodiment of the invention $R^1$ denotes 2-phenylethyl and $R^2$ denotes propyl or $R^1$ denotes propyl and $R^2$ denotes 2-phenylethyl.

The group $R^3$ is preferably selected from among methyl, ethyl, propyl, butyl, benzyl and tri-($C_{1-4}$-alkyl)-silyl, while ethyl and tert.-butyl are particularly preferred. Most particularly preferably, $R^1$ denotes phenylethyl, $R^2$ denotes propyl and $R^3$ denotes ethyl or tert.-butyl.

In the present invention the term alkyl groups, including those which are part of other groups, unless otherwise specified, denotes branched and unbranched alkyl groups with 1 to 8, preferably 1 to 6, particularly 1 to 4 carbon atoms. Examples include the following hydrocarbon groups: methyl, ethyl, propyl, 1-methylethyl (isopropyl), n-butyl, 2-methylpropyl (iso-butyl), 1-methylpropyl (sec-butyl), 1,1-dimethylethyl (tert.-butyl). The definitions propyl and butyl also include the isomeric forms. In some cases the common abbreviations Me for methyl, Et for ethyl, prop for propyl and but for butyl may also be used for the above-mentioned alkyl groups.

In the present invention the term haloalkyl groups, even if they are part of other groups, unless otherwise specified, refers to branched and unbranched haloalkyl groups with 1 to 4 carbon atoms in which at least one hydrogen atom is replaced by a halogen atom. Preferred are haloalkyl groups of the formula

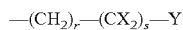
—$(CH_2)_r$—$(CX_2)_s$—Y wherein r denotes 0, 1, 2 or 3, s denotes 1, 2, 3 or 4, and the sum of (r+s) is 1, 2, 3 or 4, X denotes fluorine or chlorine and Y denotes X or H.

The following halogenated hydrocarbon groups are mentioned by way of example: trifluoromethyl, difluoromethyl, 2,2,2-trifluorethyl, 2,2,2-trichlorethyl, 2,2-dichlorethyl, 2-chloroethyl, pentafluorethyl and 1,1,1-trifluorprop-2-yl.

The cycloalkyl group according to the invention denotes a saturated cyclic hydrocarbon group with 3 to 8 carbon atoms. Cyclic hydrocarbons with 3 to 6 carbon atoms are preferred. Examples include cyclopropyl, cyclobutyl, cyclopentyl, cyclohexyl, cycloheptyl and cyclooctyl.

Alkyloxy, which may optionally also be referred to as alkoxy, denotes within the scope of the invention a straight-chain or branched alkyl group bound via an oxygen atom and having 1 to 8, preferably 1 to 6, more particularly 1 to 4 carbon atoms. The method group is particularly preferred.

The term aryl denotes an aromatic ring system with 6 to 10 carbon atoms. Preferred aryl groups are naphthyl and phenyl, the phenyl group being particularly preferred. Optionally, naphthyl is abbreviated to Naph and phenyl to Ph.

By aryl-alkylene or alkylene-aryl are meant according to the invention aryl groups which are linked via an alkylene group with 1 to 8, preferably 1 to 6, more particularly 1 to 4 carbon atoms, the above-mentioned definitions applying to alkylene groups and aryl groups. Preferred alkylene-aryl groups according to the invention, unless otherwise specified, are benzyl, 2-phenylethyl and 3-phenylpropyl.

Halogen within the scope of the present invention denotes fluorine, chlorine, bromine or iodine, while fluorine, chlorine and bromine are preferred unless otherwise specified.

The process according to the invention will now be explained in detail with reference to the three steps of the process:

Step (1):

Synthetic production of a racemic mixture of a 5-hydroxy-3-ketoester of formula A is achieved according to the invention by Aldol-Addition and is illustrated in the following Diagram 3:

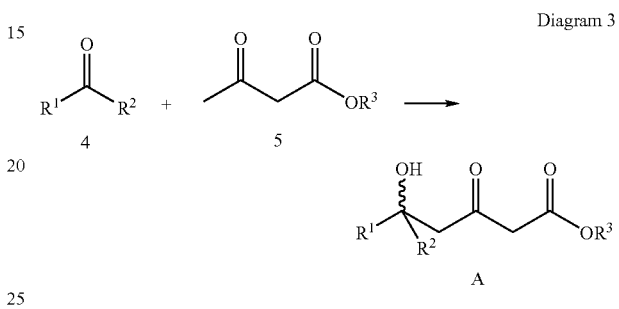

Diagram 3

For this, a suitably substituted carbonyl compound 4, wherein the groups $R^1$, $R^2$ have the meanings given hereinbefore, is reacted with an acetoacetic acid derivative 5 in which $R^3$ denotes a group selected from among $C_1$–$C_8$-alkyl, $C_1$–$C_4$-haloalkyl, $C_6$–$C_{10}$-aryl-$C_1$–$C_8$-alkylene and trihydrocarbylsilyl, to obtain the racemate A.

This reaction is carried out in the presence of strong organic or inorganic bases, preferably in the presence of strong organic bases. Strong bases for the purpose of the present invention include hydrides such as for example sodium hydride, potassium hydride and calcium hydride, amides such as lithium amide or sodium amide, organometallic compounds such as n-butyllithium, tert-butyllithium or phenyllithium, and alkali metal salts of secondary amines such as for example lithium, sodium and potassium salts of secondary amines. Preferred bases of this type are selected from among sodium hydride, n-butyllithium, lithiumdiisopropylamine, lithiumdiethylamine, lithiumhexamethyldisilazane, sodiumhexamethyldisilazane, potassiumhexamethyldisilazane or lithium-tert butoxide, preferably lithiumdiisopropylamine, lithiumdiethylamine, ithiumhexamethyldisilazane, sodiumhexamethyldisilazane, potassiumhexamethyldisilazane, most preferably lithiumdiisopropylamine and lithiumdiethylamine. These bases are either commercially available or may be synthesised using methods known in the art.

In order to prepare the racemic mixture of the 5-hydroxy-3-ketoesters A according to the invention, containing the enantiomeric compounds A1 and A2, one of the above-mentioned bases which is either generated in situ or used directly, is placed in a suitable organic solvent, preferably in an organic anhydrous solvent. The solvent used is preferably an etherial solvent such as tetrahydrofuran (THF), methylethylether, diethyl ether, tert.-butyl-methylether (TBME), dioxane or other non polar organic solvents such as toluene, hexane or heptane. If desired, the etherial solvents may also be used in admixture with the above-mentioned non polar solvents. It is preferable to use the above-mentioned etherial solvents. The solvents THF, TBME and hexane are of particular importance. If mixtures are used they are preferably THF/hexane or THF/toluene.

Within the scope the present invention it may be advantageous in certain circumstances to use organic bases of this kind in the presence of complexing co-solvents.

Such co-solvents are selected for example from among hexamethyl phosphamide (HMPT), 1,8-diazabicyclo[5.4.0]undec-7-ene (DBU) and 1,5-diazabicyclo[4.3.0]non-5-ene (DBN).

The solution thus obtained is cooled, preferably to a temperature of less than about 30° C., preferably to less than about 0° C., most preferably to less than −10° C. Particularly preferably according to the invention the reaction is carried out in the range from about 20 to −70° C., particularly from about 0 to −40° C. If one of the above-mentioned solvents is no longer in the liquid aggregate state at these temperature, the lowest possible reaction temperature is determined by the flow point or melting point of the solvent used, as will be apparent to the skilled man.

Then the acetoacetic acid derivative 5 in which $R^3$ is as hereinbefore defined is added to the cooled solution of the base in one of the above-mentioned solvents.

After the addition of 5 the mixture is stirred for about 5 minutes to 1 hour at constant temperature and a solution of 4 in one of the above-mentioned solvents, preferably in the same organic solvent in which the base is dissolved, is slowly added dropwise.

At least about 1.8 mol of base are used per mol of compound 5 used. Preferably the molar ratio of the base to 5 is in the range from about 1.8:1 to 3:1, more particularly 1.9:1 to 2.5:1, particularly about 2:1.

At about about 0.5 mol of 5 are used per mol of compound 4 put in. Preferably the molar ratio of 4 to 5 is the range from about 2:1 to 1:5, more preferably 1:1 to 1:2.5, especially about 1:1.5.

After the addition has ended stirring is continued either at constant or at slightly elevated temperature. If the temperature is elevated it is nevertheless kept below about 20° C., preferably below 0° C., more preferably below about −10° C. Most preferably according to the invention the temperature is then adjusted to a range from about +20° C. to −78° C. The reaction time is generally in the range from about 0.5–8 hours, preferably about 1–5 hours, more preferably about 1.5–3 hours.

The reaction may be stopped using methods known in the art, for example by the addition of aqueous solutions such as aqueous ammonium chloride solution. Two phases are formed. The aqueous phase is separated off. The solvent is distlled off in vacuo from the organic phase remaining. The product is worked up specifically analogously to procedures known in the prior art.

In this way the racemic mixture A of the 5-hydroxy-3-ketoester is obtained.

In another particularly preferred process the racemic mixture A of the 5-hydroxy-3-ketoester may be prepared according to German patent DE 101 08 471 C1, the disclosure of which, particularly that of Example 1, is hereby incorporated herein by reference, by reacting the dianion 5' of the acetoacetic ester 5

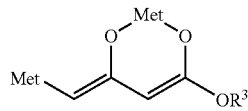

wherein Met in each case independently denote an alkali metal, with the ketone 4 in a microreactor.

Step (2):

By the process according to the invention the racemic mixture A obtained in Step 1 is then separated into the two enantiomeric 5-hydroxy-3-ketoesters A1 and A2 by preparative HPLC using a chiral carrier material in virtually quantitative yields.

The HPLC-System (High Performance Liquid Chromatography) system used may be a known apparatus. Such apparatus comprise at least one pump with a supply of eluant, a sample delivery system, at least one separating column, a detector such as a UV detector and a recording system. Currently separating systems of this kind are controlled by computer equipment with suitable software which causes the valves to open and close, the pumps to start and stop and the sensor reading to be taken. Not only are the parameters set and monitored but frequently also evaluation in terms of retention times (qualitative measurement) and the peak areas (quantitative measurement) is carried out using suitable software. HPLC technology is thus suitable for serial analysis with high precision requirements.

The columns generally have an internal diameter of between about 1 mm and 3 m, preferably between 50 mm and 1.5 m and a length of between about 1 cm and 10 m, consist of steel or pressure-resistant glass and are packed with a stationary phase.

When using an HPLC system according to step (2) of the process according to the invention, internal column diameters in the range from about 20 cm to 150 cm, preferably 30 cm to 120 cm, particularly from about 35 cm to about 100 cm, are used, the use of a chiral carrier material as stationary phase being of essential importance. The chiral carrier material used according to the invention is based on a polysaccharide which is chemically modified so that it is optically active. One example of this involves chemically binding one or more optically active groups to the basic polysaccharide structure. Particularly preferably, the polysaccharide is selected from dextrine, cyclodextrine, starch, amylose and cellulose.

The chiral carrier materials preferably used are thus tris(3,5-dimethyl-phenylcarbamate)-amylose, tris[(S)-α-methylbenzylcarbamate]-amylose, tris(3,5-dimethylphenyl-carbamate)-cellulose, tris(4-methylbenzoate)-cellulose, cellulose triacetate, cellulosetribenzoate, tris(phenylcarbamate)-cellulose, tris(4-chlorophenylcarbamate)-cellulose, cellulosetricinnamate and cellulosetribenzoate, of which tris(3,5-dimethylphenyl-carbamate)-amylose and tris(3,5-dimethylphenylcarbamate)-cellulose are most particularly preferred.

The chiral carrier material used in the present invention makes it possible to separate the racemate virtually quantitatively into the two enantiomers, obtaining the chiral products with a high enantiomeric purity of more than at least 95% e.e. (enantiomer excess), preferably 96 to 100% e.e., particularly 98.2 to 99.9% e.e. In addition, the carrier material is characterised by its long period of use while remaining of high quality as it can be used for separation in the HPLC apparatus for months, for example, and can also easily be used in a continuously operating apparatus.

The mobile phase (eluant or flow agent) used is a solvent or mixture of solvents. According to the invention, polar or nonpolar solvents may be uased as the mobile phase. Suitable organic solvents include for example acetonitrile, propionitrile, butyronitrile, methylene chloride, chloroform, hexane, iso-hexane, heptane, methylacetate, ethyl acetate, n-butylacetate, tert-butylmethylether, isopropanol, tetrahydrofuran, dioxane, methanol, ethanol, butanol, toluene, methylene chloride, chloroform, methylacetate, ethyl acetate, n-butylacetate and water and mixtures thereof while in an isocratic system, i.e. an apparatus in which only one eluant is used, ethanol, methanol, butanol and iso-hexane have proved particularly advantageous. It is particularly preferable to use mixtures of at least two solvents, in which preferably a polar solvent is mixed with a nonpolar solvent. Examples of this are iso- and/or n-hexane/ethanol, iso- and/or n-hexane/methanol and iso- and/or n-heptane/butanol. The ratio of polar to nonpolar solvent depends on the polarity of the substrate which is to be separated and the column material and is generally in the range from about 1:100 (v/v) to about 100:1 (v/v), preferably about 10:90 (v/v) to about 90:10 (v/v).

It is particularly preferred to use tris(3,5-dimethylphenyl-carbamate)-amylose with the eluant methanol and tris(3,5-dimethylphenylcarbamate)-cellulose with the eluants iso-hexane/ethanol or iso-hexane/butanol.

The other parameters of the HPLC system such as the flow rates, quantities used, temperature, pressure, etc. depend on the particular racemate which is to be separated. They may be determined easily by the average skilled man using a few tests for guidance and may be adjusted and optimised for individual cases.

The chromatographic process in step (2) of the invention may be carried discontinuously or continuously, the latter being preferable for economic reasons.

It is also possible to use a modified variant of the HPLC system such as for example the technology of SMB Chromatography (Simulated Moving Bed Chromatography). This is a concept known in the art, in which a continuous counter flow is simulated between a mobile and a stationary phase and efficient separation can be achieved in this manner in a relatively short running time. Several columns arranged one behind the other are used, with relatively short lengths, packed with relatively small particles and having short switch over times between the individual columns. The material is fed in continuously and split into two product currents with which separation is carried out. The principle details of systems of this kind are known in the art and require no further explanation.

Purely by way of example a possible construction of an SMB System will not be described with reference to FIG. 1:

The SMB-System is divided into four zones (I to IV), using 8 columns (Nr. 1 to 8), two of which always define one zone. Zone I is the SMB section which is between the addition of eluant (solvent, mobile phase) and the extract outlet. Zone II is adjacent to the extract outlet and ends at the feed inlet (addition of the material for separation). Zone III is a range between the feed inlet and the outlet for Refined product and Zone IV is adjacent to the outlet for Refined product and extends as far as the eluant inlet. Thus, the eluate flows from Zone I to Zone IV. The Refined product is the desired enantiomer while the extract is the other enantiomer.

Appropriately, the flow rate in Zone I is sufficiently high to ensure that the mobile phase goes into Zone II, whereas the flow rate in Zone IV is set low so that Refined product can be removed.

Depending on the particular separation problem the number of runs (number of cycles) is modified, as well as the flow rate in the four zones of the SMB System (ml/min), the inlet and outlet flow rate (for the eluant, extract, feed and Refined product), resulting overall in an average flow rate of the system (ml/min), the concentration of the mixture to be separated (feed in g/l), the run time per cycle (min), the maximum pressure during separation (bar), the quantity and nature of the stationary and mobile phases. It is readily possible for the skilled man to adjust the above parameters in order to achieve the highest possible purity of enantiomer.

Without being restricted to this it is particularly advantageous according to the invention to set the condtions for an SMB System to the following ranges:

| Number of columns: | about 2 to 10; |
|---|---|
| Inner diameter of column: | about 0.1 to 300 cm; |
| Length of column: | about 1 cm to 10,000 cm; |
| Chiral stationary phase: | chiral carrier material with a particular size of about 3 to 50 μm; |
| Mobile phase: | solvent or mixture of solvents; |
| Average flow rate: | about 0.1 to 10,000 ml/min; |
| UV-Detection: | at about 200 to 300 nm; |
| Temperature: | about 20 to 60° C.; |
| Pressure measured: | about 10 to 50 bar. |

The productivity of the apparatus is then obtained for example in g of enantiomer/day/kg of chiral stationary phase.

Even with an SMB apparatus of this constructon it is possible to achieve, in step (2) of the process according to the invention, separation of the racemic mixture A into the two enantiomers A1 and A2, in each case with an enantiomeric purity for the desired enantiomer of at least 98% e.e., preferably at least 99% e.e., more particularly above 99.5% e.e.

Step (3):

After the separation of enantiomers, one of the enantiomeric 5-hydroxy-3-ketoesters A1 or A2 is cyclised using known methods to obtain an optically active dihydropyrone of formula B according to Diagram 4:

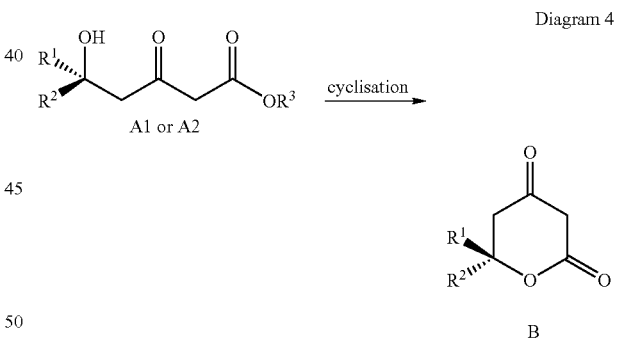

Diagram 4

This is an intramolecular transesterification, i.e. a lactone formation which is usually carried out in a slightly acidic or alkaline solution. Alkaline solutions are predominantly used when $R^3$ denotes straight chained alkyl, haloalkyl or benzyl. Bases which may be used include for example: alkali- and/or alkaline earth metal hydroxides, alkali- and/or alkaline earth metal carbonates and ammonia.

Acids are predominantly used when $R^3$ denotes branched alkyl or trihydrocarbylsilyl. Suitable acids are inorganic Brønsted-acids such as for example hydrofluoric acid, hydrochloric acid, hydrogen bromide, sulphuric acid or phosphoric acid, Lewis-acids such as for example boron trifluoride or aluminium chloride and organic acids such as for example trifluoroacetic acid, p-toluenesulphonic acid, camphorsulphonic acid and citric acid. Suitable solvents are alcohol such as methanol, ethanol or propanol, ethers such THF, dioxane, TBME or diethyl ether, optionally halogenated hydrocarbons such as hexane, toluene, dichloromethane or tetrachloromethane and water, or mixtures of the above solvents.

The reaction is carried out simply by adding a corresponding acid or base, after which the reaction is left for the necessary reaction time, preferably at ambient temperature, for example by leaving the reaction mixture to stand for a suitable length of time, optionally with stirring. The mixture is worked up in known manner.

As this is a reaction familiar to the skilled man, no further details are required. Reference is made to the preparative examples.

The process according to the invention thus makes it possible to obtain by a simple method enantiomers which were hitherto very difficult to obtain and can be carried out on a large industrial scale with excellent cost/benefit ratios. The method developed according to the invention also allows the desired product to be obtained not only in high yields but with a very high enantiomeric purity, so that the product can be successfully further processed to form an important category of pharmaceuticals.

Because of the central importance of the optically active dihydropyrones as starting compounds for synthesising optically active, pharmaceutically effective compounds, another aspect of the invention relates to the use of compounds of general formula A, A1 or A2 for preparing pharmaceutically active compounds. Preferably, the present invention relates to the use of compounds of formula A1 or B wherein $R^1$ denotes 2-phenylethyl and $R^2$ denotes propyl, for preparing Tipranavir.

The advantages conferred by the invention are many and varied. The process according to the invention gives an easy method of obtaining enantiomers which were hitherto relatively difficult to produce, on a large technical scale with excellent productivity. The process according to the invention enables the desired product to be obtained not only in high yields but also with very high enantiomeric purity, without the need for any complicated stereo selective synthesis, but proceeding via the racemic mixture which is easily obtainable. No additional purification steps are needed between the individual steps of the process, the products can be further used directly in the form in which they are obtained. In step (2) a standard HPLC apparatus can be used and the chromatographic separation may be carried out continuously or discontinuously. It is also possible to use modified methods such as SMB chromatography, thus achieving even better results in the chromatographic separation. Starting from the racemic mixture it is surprisingly possible to achieve separation into the two enantiomers with an enantiomeric purity of the desired enantiomer in excess of about 99.5% e.e., not only on an industrial scale but also in large industrial plant, to the desired extent.

In this way it is possible to obtain a category of important pharmaceutical substances, the non-peptidic HIV protease inhibitors such as Tipranavir, which means that the technical teaching of the invention is a valuable asset to the pharmaceutical sector.

The invention will hereinafter be described with reference to examples which are not intended to restrict the teaching according to the invention. Further embodiments will become apparent to the skilled man within the scope of the disclosure according to the invention.

EXAMPLE 1

The racemic mixture of ethyl 5-hydroxy-5-(2-phenylethyl)-3-oxooctanoate (1) was prepared as follows:

A mixture of 260 ml (2.5 mol) of diethylamine and 500 ml of tetrahydrofuran was placed at ambient temperature under nitrogen. It was cooled to an internal temperature of −30° C. At this 1.000 ml (2.5 mol) of n-butyllithium in n-hexane was added dropwise. The mixture was stirred for 15 minutes and 158 ml (1.25 mol) of acetoacetate was added. After another 10 minutes stirring a mixture of 150 g (0.85 mol) of 1-phenyl-3-hexanone and 100 ml THF was added dropwise. At −30° C. the mixture was stirred for a further 2 hours. The reaction solution was added to 1300 ml of saturated $NH_4Cl$ solution. The aqueous phase was separated off and the organic phase was shaken once with 500 ml of saturated $NH_4Cl$ solution and about 300 ml of 2N HCl. The aqueous phase was separated off and the organic phase was shaken once with 300 ml of saturated $NaHCO_3$ solution. The organic phase was separated off again and evaporated down in vacuo.

Yield: 296 g (>100% of theory; Theory=260.4 g), NMR: 80% purity, MS: $MH^+$=307, $(M-H)^-$=305

EXAMPLE 2

The racemic mixture of tert butyl 5-hydroxy-5-(2-phenylethyl)-3-oxooctanoate L2) was prepared as follows:

A mixture of 260 ml (2.5 mol) of diethylamine, 150 ml (1.25 mol) of 1,3-dimethyltetrahydro-2(1H)-pyrimidone (DMPU) and 500 ml of THF was prepared under nitrogen. It was cooled to an internal temperature of −15° C. and at −15 to −10° C. 1.000 ml (2.5 mol) of n-butyllithium in n-hexane was added dropwise. Then at the same temperature 207 ml (1.25 mol) of tert butyl acetoacetate was added dropwise within 1 hour. 150 ml (0.85 mol) of a solution of 1-phenyl-3-hexanone and 100 ml of tetrahydrofuran were then added dropwise within 1 hour and the mixture was stirred for 30 minutes. The cooled reaction solution was then added to 3.000 ml of saturated sodium bicarbonate solution and the upper organic phase was separated off. The aqueous solution was discarded and the organic phase was again extracted with 3.000 ml of 2N hydrochloric acid and then with 3.000 ml of water. It was then evaporated to dryness in vacuo.

NMR: 88% purity

EXAMPLE 3

The racemic mixture of the 5-hydroxy-3-ketoethylester (1) of Example 1 was resolved into the two enantiomeric forms using an SMB System. The SMB System contained 8 columns each with an internal diameter of 1 cm and 10 cm long. The columns were packed under the following conditions:

| | |
|---|---|
| chiral stationary phase: | Chiralpak ® AD (tris(3,5-dimethylphenylcarbamate)-amylose) |
| solvent: | isopropanol |
| Pressure: | 300 bar |

The columns were then equilibrated with the mobile phase methanol and tested under the following conditions:

| | |
|---|---|
| Sample: | 10 µl of Trögers base (1 g/l) and TTBB (1,3,5,-tri-tert.-butylbenzene 97%) (0.7 g/l) |
| Flow rate: | 4 ml/min |
| Pressure: | 28 bar |
| UV-Detection: | 250 nm |
| T °C.: | 25° C. |

The average flowrate in the system was 279.3 ml/min; 35 bars of pressure were measured in the system.

The individual values were: $Flowrate_{zone\ I}$=13.00 ml/min; $Flowrate_{Extract}$=3.9 ml/min; $Flowrate_{zone\ II}$=9.10 ml/min, $Flowrate_{Feed}$=0.12 ml/min, $Flowrate_{zone\ III}$=9.22 ml/min, $Flowrate_{Refined\ product}$=1.14 ml/min, $Flowrate_{zone\ IV}$=8.08 ml/min, Feed=100 g/l and ΔT (maximum temperature measured)=80.

The desired enantiomer was obtained in a purity of 99.40% e.e. (Refined product).

The other enantiomer was isolated with a purity of 96.70% e.e. (Extract).

EXAMPLE 4

The racemic mixture of the 5-hydroxy-3-ketoethylester (1) of Example 1 was resolved into the two enantiomeric forms using an SMB System. The SMB System contained 8 columns each with an internal diameter of 1 cm and a length of 10 cm. The columns were packed under the following conditions:

| | |
|---|---|
| chiral stationary phase: | Chiralcel ® OD (tris(3,5-dimethylphenylcarbamate)-amylose) |
| solvent: | isopropanol |
| Pressure: | 300 bar. |

The columns were then equilibrated with the mobile phase iso-hexane/isopropanol 90/10 and tested under the following conditions:

| | |
|---|---|
| Sample: | 10 µl TSO (trimeprazine sulphoxide) (2 g/l) + TTBB (1 g/l) |
| Flowrate: | 4 ml/min |
| Pressure: | 21 bar |
| UV-Detection: | 250 nm |
| T °C.: | 25° C. |

All the samples were then analysed under the following conditions:

| | |
|---|---|
| mobile phase: | iso-hexane/ethanol 98/2 |
| Carrier: | Chiralcel ® OD (10 µm 250 * 4.6 mm) |
| Flowrate: | 0.5 ml/min |
| UV-Detection: | 220 nm |
| Sample injection: | 10 µl |
| T ° C. | 25° C. |

The pressure measured was 23 bar.

The individual values were: $Flowrate_{zone\ I}$=18.67 ml/min; $Flowrate_{Extract}$=11 ml/min; $Flowrate_{zone\ III}$=7.67 ml/min, $Flowrate_{Feed}$=0.11 ml/min, $Flowrate_{zone\ II}$=7.78 ml/min, $Flowrate_{Refined\ product}$=1.65 ml/min, $Flowrate_{zone\ IV}$=6.13 ml/min, Feed=100 g/l, ΔT=203.5.

To avoid overloading the column a 50% lower feed flowrate was used to begin with.

The desired enantiomer was obtained in a purity of 99.64% e.e. (Refined product). The other enantiomer could be isolated with a purity of 99.15% e.e. (Extract).

EXAMPLE 5

The racemic mixture of the 5-hydroxy-3-ketoethylester (1) in Example 1 was resolved into the two enantiomeric forms using an SMB System. The SMB System contained 8 columns each with 1 cm internal diameter and 10 cm long.

The columns were packed under the following conditions:

| | |
|---|---|
| chiral stationary phase: | Chiralcel ® OD |
| solvent: | isopropanol |
| Pressure: | 300 bar. |

The columns were then tested as in Example 4:

| | |
|---|---|
| Sample: | 10 µl TSO (2 g/l) + TTBB (1 g/l) |
| Flowrate: | 4 ml/min |
| Pressure: | 21 bar |
| UV-Detection: | 250 nm |
| T °C.: | 25° C. |

All the samples were analysed under the following conditions:

| | |
|---|---|
| mobile phase: | iso-hexane/butan-1-ol 90/10 |
| Carrier: | Chiralcel ® OD (10 µm 250 * 4.6 mm) |
| Flowrate: | 1 ml/min |
| UV-Detection: | 220 nm |
| Sample injection: | 10 µl |
| T °C.: | 25° C. |

To avoid overloading the column a lower feed flowrates was used to begin with.

Under the initial conditions the pressure was about 15 bar. The different flowrates were increased in order to obtain a pressure of about 21 bar.

The individual values were: $Flowrate_{zone\ I}$=19 ml/min; $Flowrate_{Extract}$=10.50 ml/min; $Flowrate_{zone\ II}$=8.50 ml/min, $Flowrate_{Feed}$=0.09 ml/min, $Flowrate_{zone\ III}$=8.59 ml/min, $Flowrate_{Refined\ product}$=2 ml/min, $Flowrate_{zone\ IV}$=6.59 ml/min, Feed=100 g/l, ΔT=121.2 and ΔP (maximum pressure measured)=23.

The desired enantiomer was obtained with a purity of 99.79% e.e. (Refined product). The other enantiomer could be isolated with a purity of 99.39% e.e. (Extract).

EXAMPLE 6

The racemic mixture of the 5-hydroxy-3-keto-tert.-butylester (2) of Example 2 was resolved into the two enantiomeric forms using an SMB System. The SMB System contained 8 columns with an internal diameter of 4.8 mm and a length of 10 cm. The columns were packed under the following conditions:

| chiral stationary phase: | Chiralpak ® OD, 20 µm particle size |
|---|---|
| solvent: | isopropanol |
| Pressure: | 300 bar |

The columns were then rinsed out the with the mobile phase isopropanol and tested under the following conditions:

| Sample: | TSO (about 3 g/l) + TTBB (0.5 g/l) in iso-hexane/ isopropanol 90/10 - 10 µl injected in |
|---|---|
| Flowrate: | 4 ml/min |
| UV-Detection: | 250 nm |
| T ° C.: | 25° C. |

All the samples were analysed under the following conditions:

| mobile phase: | iso-hexane/ethanol 95/5 |
|---|---|
| Carrier: | Chiralcel ® OD (10 µm 250 * 4.6 mm) |
| T ° C.: | 25° C. |

The Parameters on an SMB-System with 8 columns with an internal diameter of 4.8 mm, length 10 cm, 800 g of chiral stationary phase with a feed concentration of 90 g/l were as follows:

TABLE 1

| Parameters for a 35 bar drop in pressure | Values obtained |
|---|---|
| Feed | 5.67 ml/min |
| Extract | 179.02 ml/min |
| Refined product | 57.6 ml/min |
| Eluant | 230.86 ml/min |
| Switch over time | 1.64 ml/min |
| Zone I | 464.03 ml/min |
| Zone II | 285.01 ml/min |
| Zone III | 290.77 ml/min |
| Zone IV | 233.17 ml/min |
| Average flowrate | 318.25 ml/min |
| Purity of extract | 99.36% e.e. |
| Purity of Refined product | 98.44% e.e. |
| Solvent consumption | 360.19 l/day |
| Productivity | 493.21 g of enantiomer/kg of stationary phase/day |

The desired enantiomer was accordingly obtained in a purity of 98.44% e.e. (Refined product). The other enantiomer was isolated with a purity of 99.36% e.e. (Extract).

EXAMPLE 7

The cyclisation of the desired enantiomer of the ethyl 5-hydroxy-5-(2-phenylethyl)-3-oxooctanoate (1) obtained from Examples 3 to 5 was carried out as follows:

294 g (0.864 mol) of the chiral ketoester (1) were combined with a mixture of 112 g (1.7 mol) of KOH (85%) and 600 ml of methanol at ambient temperature. The mixture was stirred overnight at ambient temperature. Then the methanol was distilled off and the residue was taken up in 600 ml of water. It was then extracted twice with 300 ml of toluene, the aqueous phase was combined with 500 ml of fresh toluene and adjusted to pH less than 2 with 290 ml of 30% of $H_2SO_4$. The product went into the toluene phase. The acidic aqueous phase was then extracted twice with 300 ml of toluene. The combined toluene phases were counter washed three times with 300 ml of water and the toluene was distilled off in vacuo.

Yield: 192 g=85.4% of theory.

Then the residue was dissolved in 580 ml of toluene and 385 ml of n-octane were added dropwise. The mixtures was stirred overnight at ambient temperature, then suction filtered and washed with 600 ml n-octane/toluene=1:1. It was dried overnight at 30° C.

Yield 156 g=69.4% of theory, melting point 99–100° C.

EXAMPLE 8

The cyclisation of the desired enantiomer of tert. butyl 5-hydroxy-5-(2-phenylethyl)-3-oxooctanoate obtained in Example 6 was carried out as follows:

3.3 g (0.01 mol) of the chiral ketoester (2) were taken up in 15 ml of trifluoroacetic acid and left to stand overnight at ambient temperature. Then excess trifluoroacetic acid distilled off and the residue was taken up in 12 ml of toluene. 8 ml of n-octane were added thereto and the mixture was stirred overnight. An oil was precipitated and the supernatant solvent was decanted off. The residue was dissolved in 6 ml of toluene and 4 ml of n-octane were added until the mixture went cloudy. A few seed crystals were added and the mixture was stirred overnight, during which time crystals were precipitated. They were suction filtered and washed with 5 ml of n-octane/toluene=1:1 and dried at 35° C. in vacuo.

What is claimed is:

1. A process for preparing an optically active 5-hydroxy-3-ketoester of the formula A1 or A2

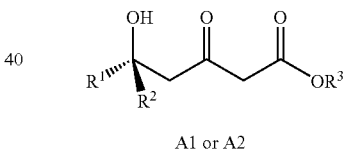

A1 or A2 or one of the tautomers thereof,
wherein
$R^1$ and $R^2$ independently of each other represent hydrogen or a group which is selected from among $C_1$–$C_8$-alkyl, $C_3$–$C_8$-cycloalkyl, $C_6$–$C_{10}$-aryl and $C_1$–$C_8$-alkylene-$C_6$–$C_{10}$-aryl, optionally with one, two or three substituents, selected from among hydroxy, halogen, $C_1$–$C_4$-alkoxy and $CF_3$, where $R^1$ and $R^2$ do not simultaneously have the same meaning, and
$R^3$ denotes a group selected from among $C_1$–$C_8$-alkyl, $C_1$–$C_4$-Haloalkyl, $C_6$–$C_{10}$-aryl-$C_1$–$C_8$-alkylene and trihydrocarbylsilyl, characterised in that a racemic mixture of a 5-hydroxy-3-ketoester of formula A

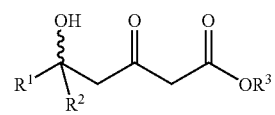

A wherein $R^1$, $R^2$ and $R^3$ are as hereinbefore defined, is resolved into the two enantiomeric 5-hydroxy-3-ketoester A1 and A2 by preparative high performance liquid chromatography (HPLC) over a chiral carrier material, wherein the chiral carrier material is selected from the group consisting of tris(3,5-dimethylphenylcarbamate)-amylose, tris[(S)-α-methylbenzvlcarbamate]-amylose, tris(3,5-dimethyphenylcarbamate)-cellulose, tris(4-methylbenzoate)-cellulose, cellulose triacetate, cellulosetribenzoate, tris(phenylcarbamate)-cellulose, tris(4-chlorophenylcarbamate)-cellulose, cellulosetricinnamate and cellulosetribenzoate.

2. The process according to claim 1, wherein the two separate enantiomeric 5-hydroxy-3-ketoesters A1 and A2 are each obtained in an enantiomer excess of at least 95%.

3. The process according to claim 1, wherein $R^1$ and $R^2$ independently of each other are selected from the group consisting of methyl, ethyl, propyl, butyl, phenyl, benzyl, phenylethyl and phenylpropyl, optionally with a substituent selected from the group consisting of hydroxy, fluorine, chlorine, bromine, method, ethoxy and $CF_3$.

4. The process according to claim 1, wherein $R^3$ is selected from the group consisting of methyl, ethyl, propyl, butyl and benzyl.

5. The process according to claim 1, wherein $R^1$ denotes 2-phenylethyl and $R^2$ denote propyl or $R^1$ denotes propyl and $R^2$ denotes 2-phenylethyl.

6. The process according to claim 1, wherein $R^3$ denotes tert.-butyl or ethyl.

7. The process according to claim 5, wherein $R^1$ denotes 2-phenylethyl, $R^2$ denotes propyl and $R^3$ denotes ethyl or tert.-butyl.

8. The process according to claim 1, wherein tris(3,5-dimethylphenylcarbamate)-amylose or tris(3,5-dimethylphenylcarbamate)-cellulose is used as the carrier material.

9. The process according to claim 1, wherein the preparative HPLC is used in the form of SMB (Simulated Moving Bed) chromatography.

* * * * *